US010405882B2

(12) United States Patent
Dolgin et al.

(10) Patent No.: US 10,405,882 B2
(45) Date of Patent: Sep. 10, 2019

(54) ACCESS SHEATH, ACCESS SYSTEM, AND RELATED METHODS

(71) Applicant: C.R. BARD, INC., Murray Hill, NJ (US)

(72) Inventors: Michael Dolgin, Cincinnati, OH (US); Matthew Winkler, Hamilton, OH (US)

(73) Assignee: C.R. BARD, INC., Murray Hill, NJ (US)

( * ) Notice: Subject to any disclaimer, the term of this patent is extended or adjusted under 35 U.S.C. 154(b) by 0 days.

(21) Appl. No.: 15/546,817

(22) PCT Filed: Feb. 23, 2016

(86) PCT No.: PCT/US2016/019149
§ 371 (c)(1),
(2) Date: Jul. 27, 2017

(87) PCT Pub. No.: WO2016/138006
PCT Pub. Date: Sep. 1, 2016

(65) Prior Publication Data
US 2018/0021059 A1    Jan. 25, 2018

Related U.S. Application Data

(60) Provisional application No. 62/119,713, filed on Feb. 23, 2015.

(51) Int. Cl.
*A61B 17/34*    (2006.01)
*A61M 29/00*    (2006.01)
(Continued)

(52) U.S. Cl.
CPC ...... *A61B 17/3423* (2013.01); *A61B 17/0218* (2013.01); *A61M 25/0009* (2013.01);
(Continued)

(58) Field of Classification Search
CPC ............ A61B 17/3423; A61B 17/0218; A61B 2090/0808; A61B 2017/00429;
(Continued)

(56) References Cited

U.S. PATENT DOCUMENTS 3,454,006 A * 7/1969 Langdon ........... A61M 25/0606
604/164.01
5,380,304 A    1/1995 Parker
(Continued)

FOREIGN PATENT DOCUMENTS

EP    2623151 A1    8/2013
WO    2010065901 A1    6/2010

OTHER PUBLICATIONS

U.S. Appl. No. 62/119,713, filed Feb. 23, 2015, Dolgin et al.
(Continued)

*Primary Examiner* — Pedro Philogene
*Assistant Examiner* — David C Comstock
(74) *Attorney, Agent, or Firm* — Dorsey & Whitney LLP

(57) ABSTRACT

Embodiments disclosed herein generally relate to an access sheath and access systems. In some embodiments, the access sheath may be non-adjustable access sheath or an adjustable access sheath. For example, a length of the adjustable access sheath may be modified or customized (e.g., before insertion thereof in a patient) to a suitable length for a particular patient. In some embodiments, the access sheath and/or dilator may have a substantially fixed or predetermined length.

40 Claims, 11 Drawing Sheets

(51) Int. Cl.
  *A61M 25/06* (2006.01)
  *A61B 17/02* (2006.01)
  *A61M 25/00* (2006.01)
  *A61B 90/00* (2016.01)
  *A61B 17/00* (2006.01)

(52) U.S. Cl.
  CPC ........ *A61M 25/0662* (2013.01); *A61M 29/00* (2013.01); *A61B 2017/00429* (2013.01); *A61B 2017/3456* (2013.01); *A61B 2090/0808* (2016.02); *A61M 25/0097* (2013.01)

(58) Field of Classification Search
  CPC ...... A61B 2017/3456; A61M 25/0009; A61M 25/0097; A61M 25/0662; A61M 29/00
  USPC ................ 600/204, 206, 208, 226; 606/191; D24/112; D8/330
  See application file for complete search history.

(56) References Cited

U.S. PATENT DOCUMENTS

| | | | |
|---|---|---|---|
| 5,700,253 A | 12/1997 | Parker | |
| 6,395,012 B1 | 5/2002 | Yoon et al. | |
| 6,447,489 B1 | 9/2002 | Peterson | |
| 6,629,534 B1 | 10/2003 | St. Goar et al. | |
| 6,702,828 B2 | 3/2004 | Whayne | |
| 6,792,979 B2 | 9/2004 | Konya et al. | |
| 7,018,401 B1 | 3/2006 | Hyodoh et al. | |
| 7,048,014 B2 | 5/2006 | Hyodoh et al. | |
| 7,320,704 B2 | 1/2008 | Lashinski et al. | |
| 7,351,247 B2 | 4/2008 | Kupiecki et al. | |
| 7,435,257 B2 | 10/2008 | Lashinski et al. | |
| 7,445,630 B2 | 11/2008 | Lashinski et al. | |
| 7,534,259 B2 | 5/2009 | Lashinski et al. | |
| 7,556,645 B2 | 7/2009 | Lashinski et al. | |
| 7,608,091 B2 | 10/2009 | Goldfarb et al. | |
| 7,658,762 B2 | 2/2010 | Lashinski et al. | |
| 7,666,204 B2 | 2/2010 | Thornton et al. | |
| 7,704,269 B2 | 4/2010 | St. Goar et al. | |
| 7,753,923 B2 | 7/2010 | St. Goar et al. | |
| 7,803,130 B2 | 9/2010 | Ryan et al. | |
| 7,815,661 B2 | 10/2010 | Mirizzi et al. | |
| 7,901,438 B2 | 3/2011 | Culbert et al. | |
| 7,935,144 B2 | 5/2011 | Robin et al. | |
| 7,972,354 B2 | 7/2011 | Prestezog et al. | |
| 7,998,151 B2 | 8/2011 | St. Goar et al. | |
| 7,998,176 B2 | 8/2011 | Culbert | |
| 8,001,974 B2 | 8/2011 | Makower et al. | |
| 8,011,370 B2 | 9/2011 | Karabey et al. | |
| 8,012,201 B2 | 9/2011 | Lashinski et al. | |
| 8,043,368 B2 | 10/2011 | Crabtree | |
| 8,187,299 B2 | 5/2012 | Goldfarb et al. | |
| 8,262,695 B2 | 9/2012 | Karabey et al. | |
| 8,308,796 B2 | 11/2012 | Lashinski et al. | |
| 8,323,334 B2 | 12/2012 | Deem et al. | |
| 8,333,201 B2 | 12/2012 | Karabey et al. | |
| 8,333,786 B2 | 12/2012 | Mirizzi et al. | |
| D673,677 S | 1/2013 | Noda et al. | |
| 8,343,031 B2 | 1/2013 | Gertner | |
| 8,353,925 B2 | 1/2013 | Makower et al. | |
| 8,377,118 B2 | 2/2013 | Lashinski et al. | |
| D679,008 S | 3/2013 | Schroeder et al. | |
| 8,398,668 B2 | 3/2013 | Makower et al. | |
| 8,409,273 B2 | 4/2013 | Thornton et al. | |
| 8,414,635 B2 | 4/2013 | Hyodoh et al. | |
| 8,465,491 B2 | 6/2013 | Yedlicka et al. | |
| 8,470,028 B2 | 6/2013 | Thornton et al. | |
| 8,574,245 B2 | 11/2013 | Garrison et al. | |
| 8,579,804 B2 | 11/2013 | Desmond, III | |
| 8,628,549 B2 | 1/2014 | To et al. | |
| D702,343 S | 4/2014 | Dale et al. | |
| D702,835 S | 4/2014 | Vinchon | |
| D703,812 S | 4/2014 | Cederschiold et al. | |
| 8,734,505 B2 | 5/2014 | Goldfarb et al. | |
| D709,753 S | 7/2014 | Guala | |
| 8,795,310 B2 | 8/2014 | Fung et al. | |
| 8,858,490 B2 | 10/2014 | Chou et al. | |
| 8,887,733 B2 | 11/2014 | Appling et al. | |
| D757,258 S | 5/2016 | Weibhaupt et al. | |
| D757,953 S | 5/2016 | Philips | |
| D760,891 S | 7/2016 | Nakamura et al. | |
| D764,660 S | 8/2016 | Babbs et al. | |
| D765,241 S | 8/2016 | Holland | |
| D794,177 S * | 8/2017 | Lebedenko .................. | D24/112 |
| 2004/0098020 A1 | 5/2004 | Nardeo | |
| 2005/0222581 A1 | 10/2005 | Fischer et al. | |
| 2006/0052750 A1 | 3/2006 | Lenker et al. | |
| 2012/0041371 A1 | 2/2012 | Tal et al. | |
| 2012/0123369 A1 | 5/2012 | Shafran | |
| 2012/0157968 A1* | 6/2012 | Eldredge ............... | A61M 15/08 604/514 |
| 2013/0226094 A1 | 8/2013 | Ahmed et al. | |
| 2014/0050208 A1 | 2/2014 | Shafran | |

OTHER PUBLICATIONS

U.S. Appl. No. 29/555,612, filed Feb. 23, 2016, Dolgin et al.
Cook Medical "Maintain protected ureteral access" Flexor Ureteral Access Sheath; www.cookmedical.com (2014) 4 pages.
International Search Report and Written Opinion from PCT International Application No. PCT/US2016/019149 dated Jul. 12, 2016.
U.S. Appl. No. 29/555,612, Oct. 3, 2017, Restriction Requirement.
U.S. Appl. No. 29/555,612, Dec. 26, 2017, Notice of Allowance.
Extended European Search Report for EP Application No. 16756195.0, dated Aug. 6, 2018.

* cited by examiner

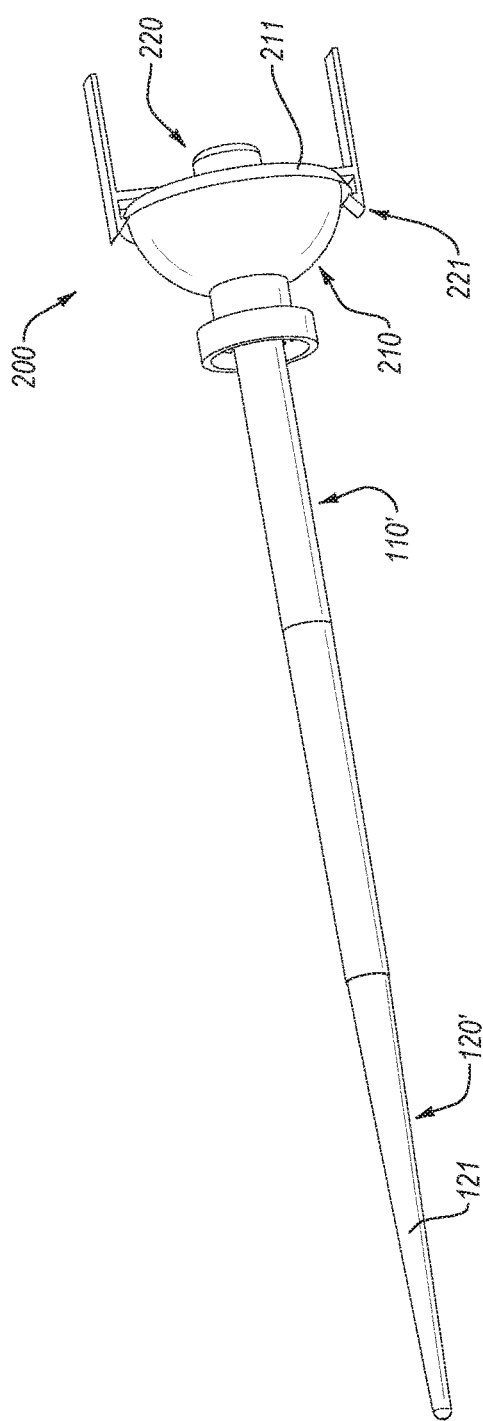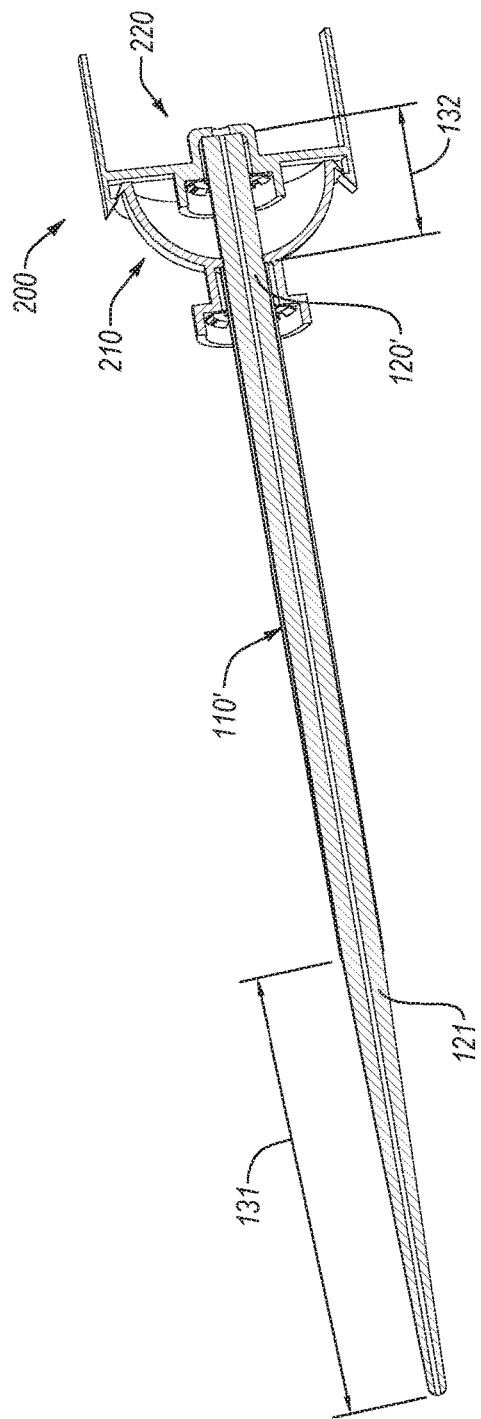
FIG. 4A
FIG. 4B

ACCESS SHEATH, ACCESS SYSTEM, AND RELATED METHODS

CROSS-REFERENCE TO RELATED APPLICATIONS

This application claims priority to U.S. Provisional Application No. 62/119,713 filed on 23 Feb. 2015, the disclosure of which is incorporated herein, in its entirety, by this reference.

BACKGROUND

Generally, various procedures may require access to a target location inside a patient's body (e.g., patient's kidney). For example, an access channel may be established and may facilitate insertion of various medical devices to the target location in the patient.

Moreover, the access channel may facilitate withdrawal of elements from the target location (e.g., kidney stones, etc.). For instance, a length of the access channel may extend from an entry location to the target location. Hence, the length of the access channel may vary from one patient to another and may depend on patient's sex, anatomy, etc.

Accordingly, users and manufacturers of catheterization systems continue to seek improved access systems to accommodate variability among patients.

SUMMARY

Embodiments disclosed herein generally relate to an access sheath and access systems. In some embodiments, the access sheath may be non-adjustable access sheath or an adjustable access sheath. For example, a length of the adjustable access sheath may be modified or customized (e.g., before insertion thereof in a patient) to a suitable length for a particular patient. For instance, the length of the adjustable access sheath may be modified at least partially based on the patient's sex, weight, general anatomy, combinations thereof, etc. In some embodiments, the user of the access system may modify or customize the length of the adjustable access sheath on as-needed basis, thereby avoiding the necessity of manufacturing and/or storing access sheaths of various lengths.

In an embodiment, an access system is disclosed. The access system includes an access handle including a wall including an interior surface defining a funnel having an opening at a proximal end of the access handle, and a lip positioned near the opening of the funnel and extending outward from an exterior surface of the wall. The access system also includes a tubular access sheath secured to the access handle, and a retainer including a plurality of clips sized and configured to clamp about the lip of the access handle. Moreover, the access system includes a dilator sized and shaped to be positioned inside the access sheath, the dilator being secured to the retainer.

In an embodiment, an access assembly is disclosed. The access assembly includes an access handle including a wall including an interior surface defining a funnel having an opening at a proximal end of the access handle, and a lip positioned near the opening of the funnel and extending outward from an exterior surface of the wall. The access assembly also includes a tubular access sheath secured to the access handle, and a retainer including a plurality of clips positioned about the lip and detachably securing the retainer to the access handle. Furthermore, the access assembly includes a dilator secured to the retainer and slidably positioned inside the access sheath.

In an embodiment, an adjustable access system is disclosed. The adjustable access system includes an adjustable access sheath including a tubular member, one or more indicators located along a length of the tubular member and configured to facilitate length-adjustment of the tubular member to a suitable length, and an adjustable dilator locatable inside the adjustable access sheath, the adjustable dilator including a tapered portion near distal end thereof.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments, wherein identical reference numerals refer to identical or similar elements or features in different views or embodiments shown in the drawings.

FIG. 4A is an isometric view of the length-adjusted adjustable sheath-dilator assembly of FIG. 2 connected to a control handle assembly, according to an embodiment;

FIG. 4B is an isometric cutaway view of the length-adjusted adjustable sheath-dilator assembly of FIG. 2 connected to a control handle assembly, according to an embodiment;

DETAILED DESCRIPTION

Embodiments disclosed herein generally relate to an access sheath and access systems. In some embodiments, the access sheath may be non-adjustable access sheath or an adjustable access sheath. For example, a length of the adjustable access sheath may be modified or customized (e.g., before insertion thereof in a patient) to a suitable length for a particular patient. For instance, the length of the adjustable access sheath may be modified at least partially based on the patient's sex, weight, general anatomy, combinations thereof, etc. In some embodiments, the user of the access system may modify or customize the length of the adjustable access sheath on as-needed basis, thereby avoiding the necessity of manufacturing and/or storing access sheaths of various lengths.

Generally, the adjustable access sheath may be inserted at an access or entry location on the patient (e.g., at an incision, into the urethra, etc.). Moreover, the adjustable access sheath may extend from the entry location to a target location (e.g., patient's kidney). In some embodiments, the adjustable access sheath may be customized to a length that may position a proximal end thereof at or near the entry location and a distal end thereof at or near the target location, such near or as inside the patient's kidney. As such, for instance, positioning the proximal end at or near the entry location may facilitation insertion of suitable tools into and/or through the adjustable sheath (e.g., toward or to the target location) and/or manipulation of the inserted tools.

Furthermore, at least one embodiment includes an adjustable dilator. For instance, the adjustable dilator may be customized together with the adjustable access sheath. The adjustable access sheath may be fitted over the adjustable dilator, such that the adjustable sheath-dilator assembly may be advanced into the patient in a manner that the dilator expands or forces outward tissue to facilitate entry of the access sheath. In some embodiments, the adjustable dilator and the adjustable access sheath may be length-adjusted in a manner that after connecting with an access handle or funnel, a distal end of the adjustable dilator may be positioned at a predetermined and/or suitable location relative to the distal end of the adjustable access sheath.

In some embodiments, the access sheath and/or dilator may have a substantially fixed or predetermined length. For example, a user may select the access sheath and dilator of a suitable length for the procedure. As described below, a control assembly may secure the access sheath and dilator at suitable and/or selected positioned relative to each other. Moreover, a portion of the control assembly may be moved relative to another portion thereof to move the dilator relative to the access sheath.

Figure 1:
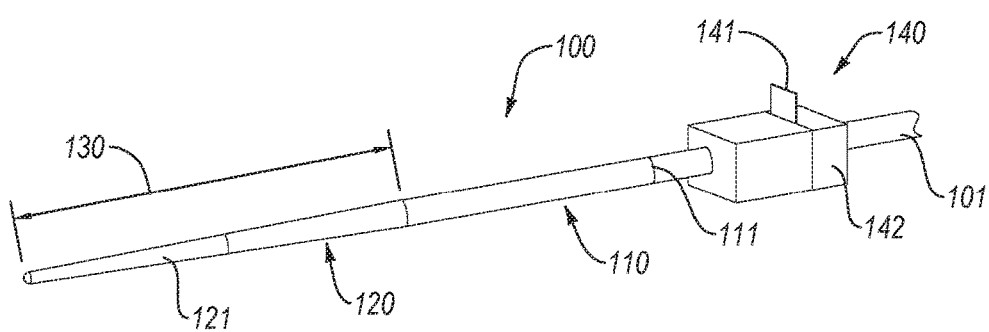
FIG. 1 is an isometric view of an adjustable sheath-dilator assembly and a cutter assembly, according to an embodiment.

In an embodiment, the access system may include a preassembled adjustable dilator and adjustable access sheath, which may be cut or trimmed to a suitable length. FIG. 1 illustrates an adjustable sheath-dilator assembly 100 that includes an adjustable access sheath 110 fitted of an adjustable dilator 120 according to an embodiment. In some embodiments, a distal end of the adjustable access sheath 110 may be offset from a distal end of the adjustable dilator 120 by an initial distal offset 130. In particular, for example, the distal ends of the adjustable access sheath 110 and adjustable dilator 120 may have the initial distal offset 130 when proximal ends thereof are approximately aligned with each other without offset.

Generally, the adjustable access sheath 110 may have a tubular shape, such that the adjustable dilator 120 may fit into the interior space thereof. For example, the adjustable access sheath 110 may be approximately cylindrical and may have an inside diameter that has a slip fit with the outside diameter of the adjustable dilator 120 (e.g., the outside diameter of the adjustable dilator 120 and the inside diameter of the adjustable access sheath 110 may have a clearance of 0.0005 inch or more). In other words, the adjustable access sheath 110 and adjustable dilator 120 may move or slide relative to each other.

Moreover, in at least one embodiment, the adjustable dilator 120 may have a generally tapered distal portion 121, which may start at a first, constant diameter that has a slip fit with the inside diameter of the adjustable access sheath 110, and continuously (and/or gradually) reduce toward a second, smaller diameter at the distal end of the adjustable dilator 120. When the adjustable sheath-dilator assembly 100 is inserted at the entry location of the patient, the tapered distal portion 121 of the adjustable dilator 120 may spread surrounding tissue to facilitate entry and advancement of the adjustable access sheath 110 together with the adjustable dilator 120. When advancing the adjustable dilator 120 together with the adjustable access sheath 110, the tapered distal portion 121 may start at a location that is distal from the distal end of the adjustable access sheath 110 (e.g., to avoid entry of tissue between the adjustable dilator 120 and adjustable access sheath 110).

In one or more embodiments, the initial distal offset 130 may be such that after adjusting the lengths of the adjustable dilator 120 and adjustable access sheath 110, the adjustable dilator 120 may be repositioned along the adjustable access sheath 110 to accommodate attachment of a control mechanism (e.g., access handle or funnel, etc.), while maintaining the distal end of the adjustable dilator 120 offset from the distal end of the adjustable access sheath 110, such that the tapered distal portion 121 is offset from the distal end of the adjustable access sheath 110 (as described below in more detail). Hence, the adjustable access sheath 110 and adjustable dilator 120 may be length-adjusted together. For instance, the adjustable sheath-dilator assembly 100 may be inserted into a cutter assembly 140 and cut or trimmed to a suitable size. That is, in some embodiments, the adjustable access sheath 110 and adjustable dilator 120 may be cut together to a suitable size.

The cutter assembly 140 may have any number of suitable configurations, which may vary from one embodiment to the next. For example, the cutter assembly 140 may include a cutter 141 (e.g., a guillotine-type cutter), which may be operated to cut through the adjustable access sheath 110 and adjustable dilator 120, thereby modifying lengths thereof as may be suitable for a particular procedure. In some embodiments, the cutter assembly 140 may include an alignment block 142, which may align the adjustable access sheath 110 and adjustable dilator 120 relative to the cutter 141 (e.g., the alignment block 142 may include an opening for aligning the adjustable access sheath and the adjustable dilator relative to the cutter 141). Furthermore, in at least one embodiment, the cutter 141 may be coupled to the alignment block 142 in a manner that permits the cutter 141 to move relative to the alignment block 142 and cut the adjustable access sheath 110 and adjustable dilator 120

In some embodiments, the adjustable access sheath 110 and/or adjustable dilator 120 may be cut or trimmed manually (e.g., with a scalpel, scissors, rotating cutter, etc.). For example, as described below, the adjustable access sheath 110 and/or adjustable dilator 120 may include markings or indicators that may identify any number of suitable cut locations along the respective lengths of the adjustable access sheath 110 and adjustable dilator 120. For instance, the adjustable access sheath 110 may include a tubular member that has one or more markings and/or other indicators that may facilitate trimming or cutting the tubular member of the adjustable access sheath 110 to a suitable size. Similarly, the adjustable dilator 120 may include a substantially cylindrical member with one or more markings or indicators that may facilitate cutting the cylindrical member of the adjustable dilator 120 to a suitable size. In some instances, the adjustable dilator 120 may be at least partially hollow and/or may include a core (e.g., a reinforcing core). It should be appreciated that, while the adjustable access sheath 110 and adjustable dilator 120 may include material suitable for cutting, the adjustable access sheath 110 and adjustable dilator 120 may have sufficient stiffness and/or compliance to facilitate insertion of the adjustable access sheath 110 and adjustable dilator 120 into the patient as well as manipulation thereof after insertion.

Generally, the adjustable sheath-dilator assembly 100 (e.g., adjustable access sheath 110 and/or adjustable dilator 120) may have any number of indicators that may aid the user in modifying adjustable access sheath 110 and adjustable dilator 120 to a suitable size. For example, the adjustable access sheath 110 may include markings 111 (e.g., lines, dots, etc.) that may be aligned with the alignment block 142, cutter 141, combinations thereof, or other suitable component or element of the cutter assembly 140. Additionally or alternatively, the adjustable access sheath 110 may include at least partially transparent or translucent material, and the adjustable dilator 120 may include markings that may be visible through the adjustable access sheath 110 and may be used for aligning the adjustable sheath-dilator assembly 100 relative to each other and/or relative to the cutter assembly 140. In any event, aligning the adjustable access sheath 110 relative to the cutter assembly 140 may facilitate cutting the adjustable access sheath 110 and adjustable dilator 120 to a suitable length (e.g., the markings may be spaced apart at predetermined distances one from another to aid in determining the length to be removed and/or the remaining length for the length-adjusted adjustable access sheath 110 and/or adjustable dilator 120).

Embodiments also may include protrusions, indents, detents, patters, combinations thereof, or other indicators or markings that may facilitate alignment of the adjustable sheath-dilator assembly 100 relative to the cutter assembly 140 and cutter 141. For example, protrusions along the length of the adjustable access sheath 110 may facilitate movement of the adjustable access sheath 110 and adjustable dilator 120 through the cutter assembly 140 at predetermined increments (e.g., by passing over an interfering element). Also, indentations in the adjustable access sheath 110 and a corresponding interference elements of the cutter assembly 140 may produce clicks and/or may resist movement of the adjustable sheath-dilator assembly 100 through the cutter assembly 140 in a manner that may aid user in identifying the length of the adjustable sheath-dilator assembly 100 that has passed through the through the cutter assembly 140, thereby facilitating positioning the adjustable sheath-dilator assembly 100 in the cutter assembly 140 for removal of a predetermined and/or suitable portion of the adjustable access sheath 110 and adjustable dilator 120 (e.g., removed portion 101).

In some embodiments, the adjustable access sheath 110 may be reinforced (e.g., may include a reinforcing member, such as reinforced core). For example, the adjustable access sheath 110 may include a metal (e.g., steel, titanium, etc.) wire overmolded or otherwise encapsulated by material that may at least partially form the interior and/or outer surfaces of the adjustable access sheath 110. In some embodiments, the reinforced adjustable access sheath 110 may be cut through the reinforcing member. Such cut, however, may expose a portion of the reinforcing member.

Additionally or alternatively, the adjustable access sheath 110 may include breaks or gaps in the reinforcing member (e.g., the adjustable access sheath 110 may include multiple reinforcing members along the length thereof). Hence, the adjustable access sheath 110 may be cut at one or more gaps between the reinforcing members. As such, one, some, or all of the reinforcing members may remain enclosed or encapsulated after cutting or otherwise length-adjusting the adjustable access sheath 110.

Moreover, as mentioned above, the adjustable access sheath 110 and/or adjustable dilator 120 may include any number of suitable indicators, which may aid the user in aligning the adjustable access sheath 110 and/or adjustable dilator 120 relative to the cutter assembly 140. In some embodiments, such indicators may align the adjustable access sheath 110 relative to the cutter assembly 140 in a manner that the cutter 141 aligns to cut the adjustable access sheath 110 at a gap between the reinforcing members. For example, the material encapsulating the reinforcing member may be transparent, and breaks or gaps between the reinforcing members may be a visible indicator that may aid the user in aligning the adjustable access sheath 110 and/or adjustable dilator 120 relative to the cutter 141. Additionally or alternatively, the adjustable access sheath 110 may include one or more markings that may be aligned with the breaks or gaps between the reinforcing members.

It should be appreciated that the adjustable access sheath 110 and/or adjustable dilator 120 may be length-adjusted with or by any number suitable mechanisms or devices, which may vary from one embodiment to the next. For instance, heating and/or melting elements may cut or pass through at least a portion of the adjustable access sheath 110 and/or adjustable dilator 120. In some embodiments, the reinforcing member(s), the adjustable access sheath 110, the adjustable dilator 120, or combinations thereof may include penetrations, holes, notches, other stress-susceptible features, etc., which may facilitate breaking or tearing the adjustable access sheath 110, the adjustable dilator 120, or combinations to adjust the lengths thereof.

Figure 2:
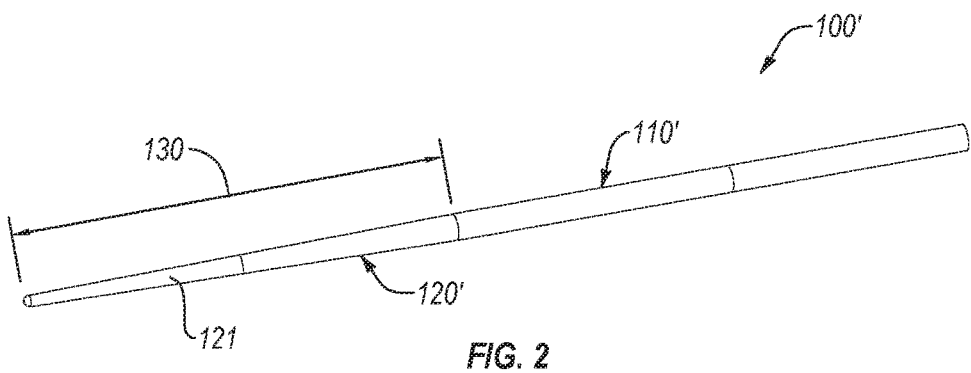
FIG. 2 is an isometric view of a length-adjusted adjustable sheath-dilator assembly, according to an embodiment.
Figure 3:
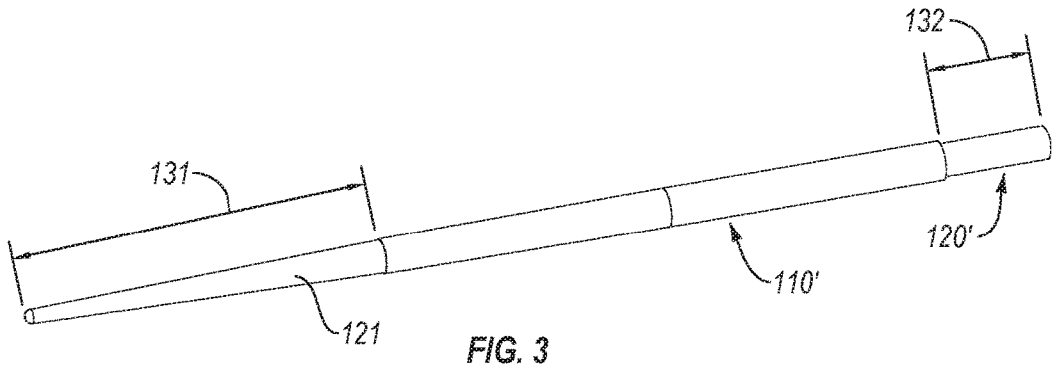
FIG. 3 is an isometric view of the length-adjusted adjustable sheath-dilator assembly of FIG. 2 with a shifted adjustable access sheath and dilator, according to an embodiment.

In any event, the adjustable sheath-dilator assembly 100 (FIG. 1) may be modified or adjusted to a suitable length by removing portions of the adjustable access sheath 110 and/or the adjustable dilator 120, to produce length-adjusted sheath-dilator assembly 100', as shown in FIG. 2, while maintaining the initial distal offset 130 between the distal ends of length-adjusted access sheath 110' and length-adjusted dilator 120'. According to at least one embodiment, the length-adjusted access sheath 110' may be advanced along the length-adjusted dilator 120' in the distal direction (e.g., reducing the offset between the distal ends thereof) to a deployment offset 131, shown in FIG. 3. Moreover, in some embodiments, the deployment offset 131 may be greater or longer than the tapered distal portion 121 of the length-adjusted dilator 120'.

As described above, in at least one embodiment, the length-adjusted access sheath 110' may be advanced along the length-adjusted dilator 120' to produce the deployment offset 131. Furthermore, the proximal ends of the length-adjusted dilator 120' and length-adjusted access sheath 110' may be offset from each other in a manner that facilitates connection of the control assembly to the length-adjusted access sheath 110' and length-adjusted dilator 120' during. In particular, the proximal ends of the length-adjusted access sheath 110' and length-adjusted dilator 120' may be offset from each other by a proximal attachment offset 132. For example, the proximal attachment offset 132 may facilitate attachment of a control assembly 200 to the length-adjusted access sheath 110' and length-adjusted dilator 120' (e.g., the adjustable access sheath 110 and the adjustable dilator 120 (FIG. 1) may be supplied without the control assembly 200, and after adjustment thereof, the control assembly 200 may be attached thereto), as shown in FIGS. 4A-4B.

As shown in FIG. 4A, in an embodiment, the control assembly 200 may include an access handle 210 that may secure the length-adjusted access sheath 110' and a retainer 220 that may secure the length-adjusted dilator 120'. For example, the retainer 220 may be connected to the access handle 210 in a manner that secures the length-adjusted dilator 120' relative to the length-adjusted access sheath 110' (e.g., the control assembly 200 may secure the length-adjusted access sheath 110' relative to the length-adjusted dilator 120' to prevent lateral and/or axial movement thereof relative to each other). The access handle 210 and/or retainer 220 may include any number of suitable mechanisms for connecting or attaching together. For instance, the access handle 210 may include a lip 211 (e.g., located near an opening or mouth of the funnel), and the retainer 220 may include retention clips 221 that may fit and/or snap over the lip 211, thereby connecting together the access handle 210 and the retainer 220 and securing the length-adjusted access sheath 110' and length-adjusted dilator 120' relative to each other.

In an embodiment, the lip 211 may extend about and partially define a periphery of the access handle 210. For example, the access handle 210 may have a wall (e.g., a semispherical or dome-shaped wall) that defines the funnel and the lip 211 may extend outward from an outer surface of the wall and around the perimeter defined by the wall. Furthermore, a user may manipulate the control assembly 200 to control the length-adjusted access sheath 110' and the length-adjusted dilator 120' (e.g., in a patient's body).

Additionally or alternatively, as shown in FIG. 4B, the control assembly 200 may maintain the deployment offset 131 between distal ends of the length-adjusted access sheath 110' and length-adjusted dilator 120'. For example, the length-adjusted access sheath 110' may be secured to the access handle 210 at a predetermined location (e.g., such that the proximal end of the length-adjusted access sheath 110' bottoms-out at a stop or bottom of a pocket in the access handle 210). Similarly, the length-adjusted dilator 120' may be secured to the retainer 220 at a predetermined location (e.g., such that the proximal end of the length-adjusted dilator 120' bottoms-out at a stop or bottom of a pocket in the retainer 220). Furthermore, after connecting together the access handle 210 and retainer 220, the proximal ends of the length-adjusted access sheath 110' and length-adjusted dilator 120' may be at the proximal attachment offset 132 from each other. In other words, the control assembly 200 may position and/or maintain the proximal ends of the length-adjusted access sheath 110' and length-adjusted dilator 120' from each other at the proximal attachment offset 132, thereby maintaining the deployment offset 131 between the distal ends of the length-adjusted access sheath 110' and length-adjusted dilator 120'. For instance, as described above, the deployment offset 131 between the distal ends of the length-adjusted dilator 120' and length-adjusted access sheath 110' may position the tapered distal portion 121 of the length-adjusted dilator 120' distally of the distal end of the length-adjusted access sheath 110'.

Figure 5:
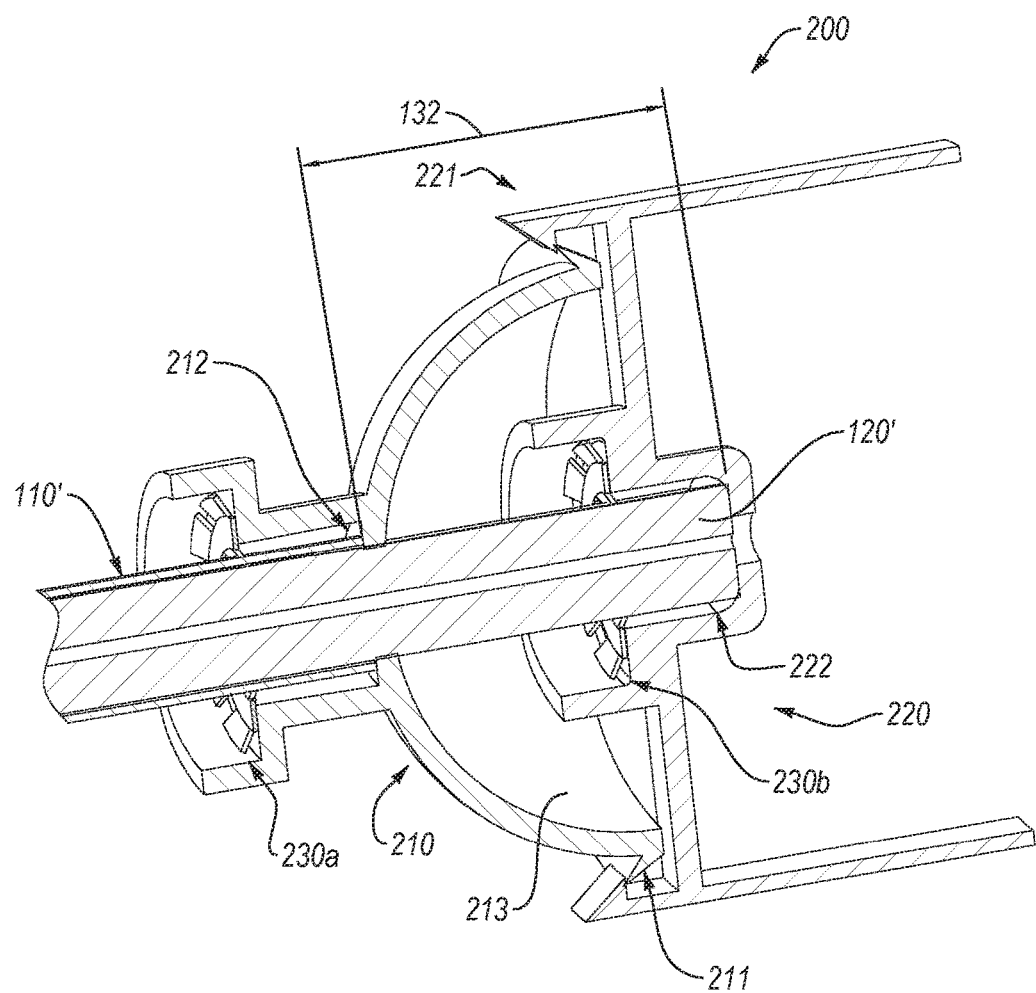
FIG. 5 is an enlarged isometric cutaway view of the handle assembly of FIG. 4B.

As shown in FIG. 5, according to at least one embodiment, the length-adjusted access sheath 110' may be secured in a handle pocket 212 of the access handle 210 (e.g., the handle pocket 212 may be positioned at distal end of the access handle 210), and the length-adjusted dilator 120' may be secured in a retainer pocket 222. More specifically, for example, the proximal end or edge of the length-adjusted access sheath 110' may abut the bottom of the handle pocket 212, and the proximal end or edge of the length-adjusted dilator 120' may abut the bottom of the retainer pocket 222. Hence, fixing the relative positions of the bottoms of the handle pocket 212 and retainer pocket 222 may fix or secure the length-adjusted access sheath 110' relative to the length-adjusted dilator 120' along respective lengths thereof. For instance, the access handle 210 and retainer 220 may secure the proximal ends of the length-adjusted access sheath 110' and length-adjusted dilator 120' at the proximal attachment offset 132 therebetween (which may produce the deployment offset 131 between the distal ends thereof (FIGS. 4A-4B)). As mentioned above, the access handle 210 may include the lip 211 and the retainer 220 may include the retention clips 221 that may snap over or otherwise secure the retainer 220 to the access handle 210.

In an embodiment, the access handle 210 may include a funnel 213 (e.g., generally tapered, spherical, etc.) at a proximal end of the access handle 210. As described below in more detail, the length-adjusted dilator 120' may be removed from the length-adjusted access sheath 110', thereby providing access to the insert tools through the length-adjusted access sheath 110' toward and/or to the target location in the patient. For instance, the retainer 220 may be detached or unlatched from the access handle 210 (e.g., by unlatching the retention clips 221 from the lip 211), and the retainer 220 may be moved proximally together with the length-adjusted dilator 120', thereby removing the length-adjusted dilator 120' from the length-adjusted access sheath 110'. In some instances, the funnel 213 may facilitate insertion of tools into the length-adjusted access sheath 110' and/or manipulation of such tools after insertion thereof.

Generally, the length-adjusted access sheath 110' and length-adjusted dilator 120' may be secured to the respective access handle 210 and retainer 220 with any number of suitable mechanisms or attachments. In at least one embodiment, the access handle 210 and retainer 220 may include retention clips 230a, 230b that may secure the length-adjusted access sheath 110' and length-adjusted dilator 120', respectively. For instance, as described below in more detail, the retention clips 230a, 230b may include inner and outer gripping members that may secure the retention clips 230a, 230b in the respective handle pocket 212 and retainer pocket 222. Moreover, the retention clips 230a, 230b may secure the length-adjusted access sheath 110' and length-adjusted dilator 120' to the access handle 210 and retainer 220, respectively.

For example, when the length-adjusted access sheath 110' is inserted into the handle pocket 212, the inner gripping members of the retention clip 230a may press against the outer diameter of the length-adjusted access sheath 110' and/or dig into the outer surface of the retention clip 230a, thereby securing the length-adjusted access sheath 110' in the access handle 210. Similarly, when the length-adjusted dilator 120' is inserted into the retainer pocket 222, the inner gripping members of the retention clip 230b may press against the outer diameter of the length-adjusted dilator 120' and/or dig into the outer surface of the retention clip 230b, thereby securing the length-adjusted dilator 120' in the retainer 220.

Figure 6A:
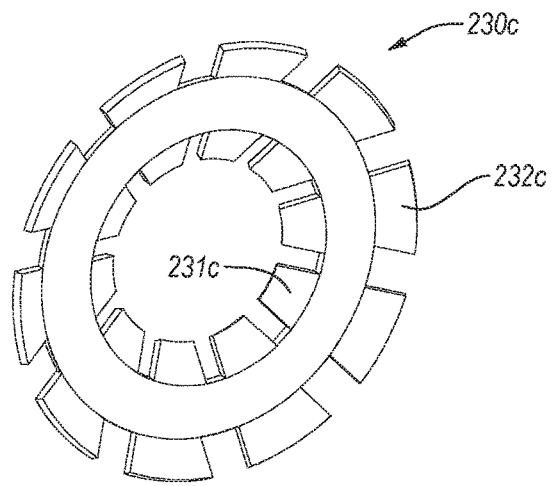
FIG. 6A is an isometric view of a retention clip, according to an embodiment.

Generally, the retention clips 230a, 230b may comprise or include any suitable material. Examples of suitable materials include, steel, brass, plastics, etc. Furthermore, in some embodiments, as shown in FIG. 6A, a retention clip 230c may include pre-bent inner gripping members 231c and outer gripping members 232c. In at least one embodiment, the inner gripping members 231c and outer gripping members 232c may be arranged generally circumferentially, in a manner that facilitates securing a cylindrical access sheath or dilator and further facilitates securing the retention clip 230c in a circular or cylindrical pocket.

In one or more embodiments, the inner gripping members 231c may be bent in the direction of the insertion of the access sheath or dilator (as applicable). Analogously, the outer gripping members 232c may be bent in a direction that is opposite to the insertion of the outer gripping members 232c into the pocket (e.g., in a direction that is opposite to the bend direction of the inner gripping members 231c). In other words, the inner gripping members 231c and outer gripping members 232c may be bent in the direction that is opposite to the respective directions in which in the inner gripping members 231c and outer gripping members 232c restrain movement.

As such, the retention clip 230c may be pressed (e.g., press-fitted) into a pocket and the outer gripping members 232c may secure the retention clip 230c therein. Moreover, the inner gripping members 231c may allow the access sheath or dilator (as applicable) to pass therebetween in the insertion direction but may prevent or impede movement of the access sheath or dilator when a force in an opposite direction is applied thereto. Additionally or alternatively, in an embodiment, the inner gripping members 231c may prevent rotation and/or shifting of the access sheath or dilator relative thereto.

Figure 6B:
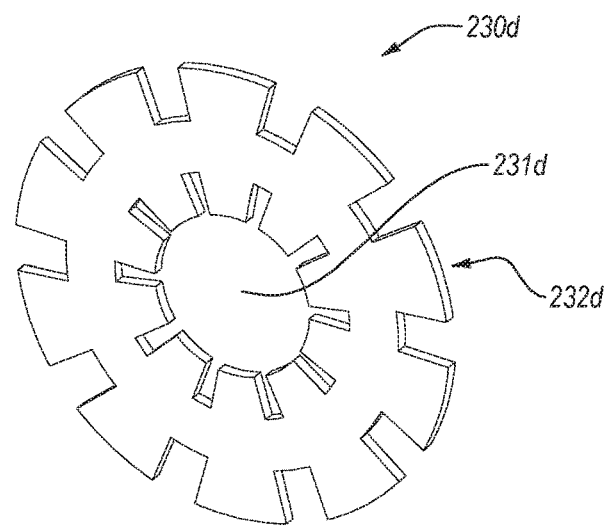
FIG. 6B is an isometric view of a retention clip, according to another embodiment.

In some instances, as shown in FIG. 6B, a retention clip 230d may include unbent inner gripping members 231d and outer gripping members 232d. For example, the inner gripping members 231d and outer gripping members 232d may be flexible and/or resilient and may flex in response to force applied thereto. For instance, the outer gripping members 232d may flex in a direction that is opposite to the direction of insertion thereof into the pocket. Analogously, the inner gripping members 231d may flex in the direction of insertion of the access sheath or dilator therebetween.

In any event, the inner gripping members 231d may secure the access sheath or dilator (as applicable), and the outer gripping members 232d may secure the retention clip 230d in a pocket or opening. It should be appreciated that the shape and size (e.g., diameter) formed or defined by or between the inner gripping members 231d and inner gripping members 231c (FIG. 6A) may vary from one embodiment to the next and may depend on the size (e.g., outside diameter) of the secured element (e.g., access sheath, dilator, etc.). Similarly, the outer gripping members 232d and outer gripping members 232c (FIG. 6A) may define an outer shape and size of the respective retention clips 230d and 230c (FIG. 6A), such as outside diameters thereof, which may vary from one embodiment to the next and may depend on the size of the pocket or opening securing the retention clips 230d and 230c (FIG. 6A).

Figure 7A:
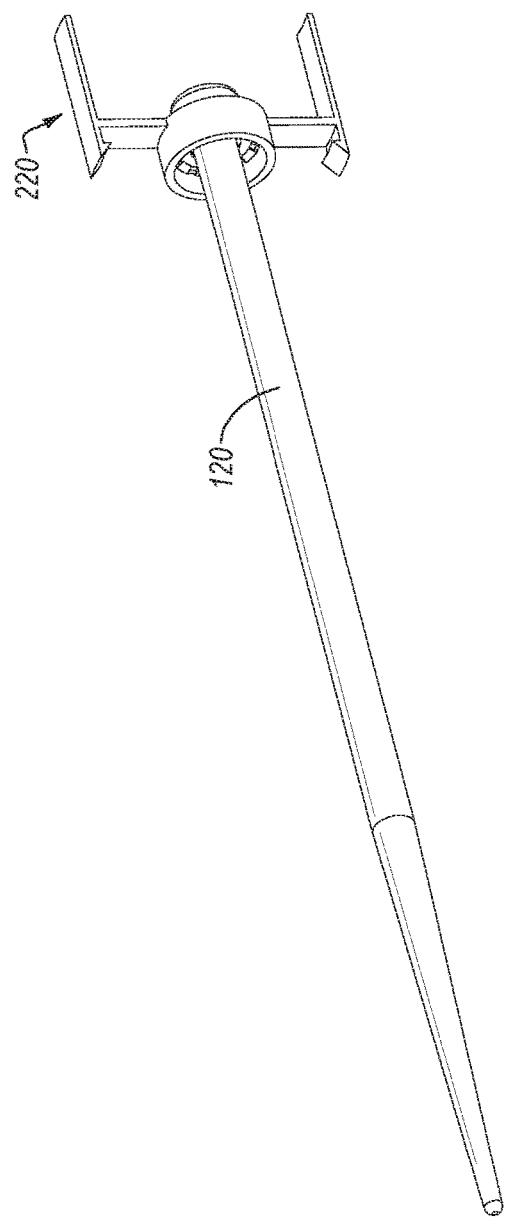
FIG. 7A is an isometric view of a dilator connected to a retainer, according to an embodiment.
Figure 7B:
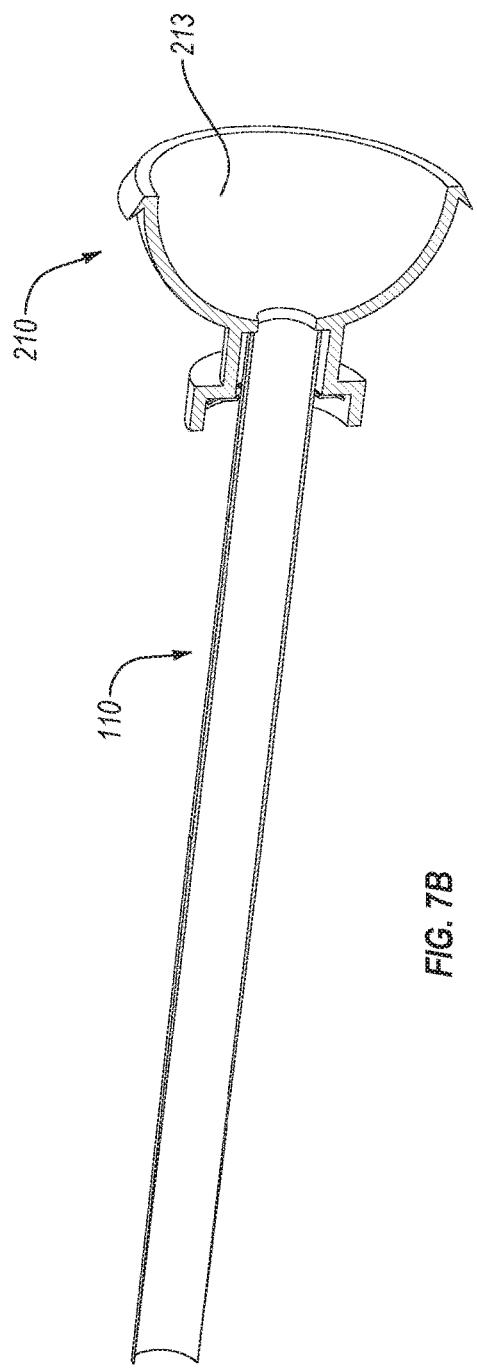
FIG. 7B is an isometric view of an adjustable access sheath connected to a access handle, according to an embodiment.

In any event, as described above, the access sheath and dilator may be secured to the access handle and retainer, respectively. As shown in FIGS. 7A-7B, the retainer 220 may be detached from the access handle 210 and, subsequently, the length-adjusted dilator 120' may be withdrawn from the length-adjusted access sheath 110'. As such, the length-adjusted access sheath 110' may provide unobstructed access (e.g., for insertion of tools, etc.) from the entry location to the target location. In addition, as mentioned above, the access handle 210 may include the funnel 213, which may facilitate insertion and control of tools or instruments in the length-adjusted access sheath 110'. In some embodiments, the length-adjusted access sheath 110' and length-adjusted dilator 120' may be cut to length or modified in a manner that may place the access handle 210 and funnel 213 at or near the access location on the patient.

Generally, the control assembly may vary from one embodiment to the next. In some embodiments, the access sheath and/or dilator may be provided or supplied in predetermined lengths (e.g., the access sheath and/or dilator may be used in a procedure without adjusting lengths thereof). As such, the cutter assembly may be unnecessary for performing a procedure, and a user may choose the access sheath and/or dilator of suitable lengths.

Figure 8A:
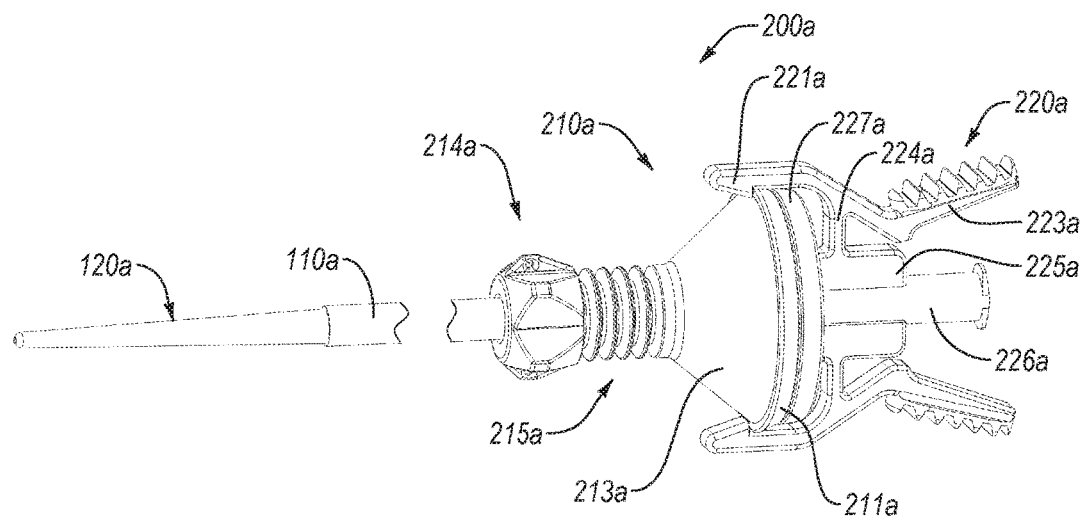
FIG. 8A is an isometric view of a sheath-dilator assembly connected to a control handle assembly, according to an embodiment.
Figure 8B:
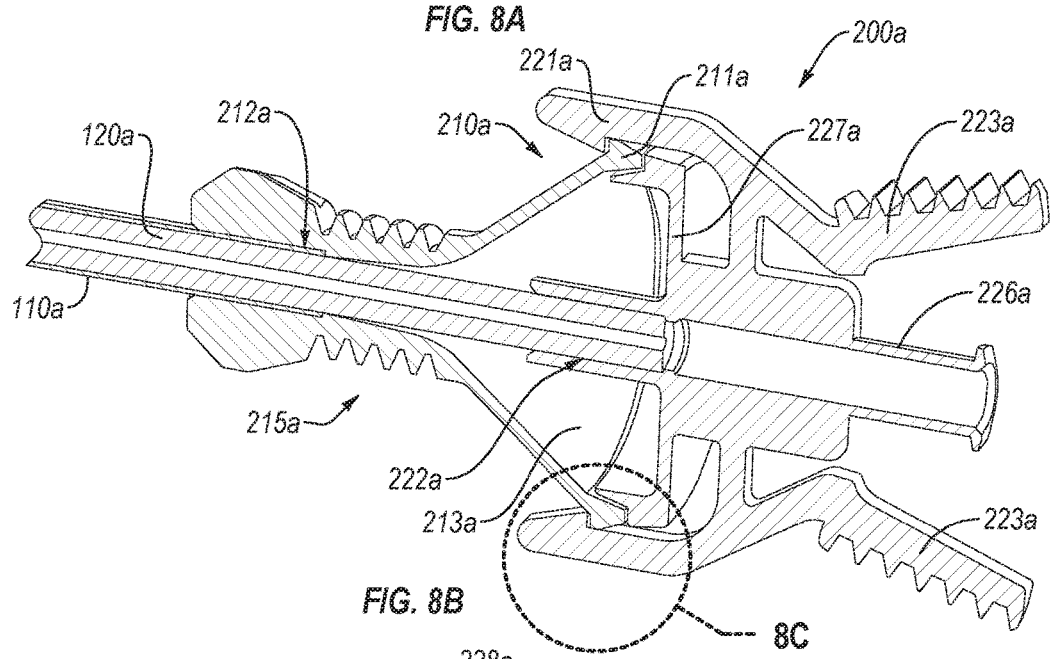
FIG. 8B is an isometric cutaway view of the sheath-dilator assembly connected to the control handle assembly of FIG. 8A.

For example, the access sheath and/or dilator may be connected to the respective portions of the control assembly without retention clips (e.g., attachment may be via press-fit, adhesive, weld, etc.). FIGS. 8A-8B illustrate a control assembly 200a connected to an access sheath 110a and dilator 120a, according to an embodiment. Except as otherwise described herein, the control assembly 200a, access sheath 110a, and dilator 120a and their respective elements and components may be similar to or the same as the respective control assembly 200, adjustable access sheath 110, length-adjusted access sheath 110', adjustable dilator 120, length-adjusted dilator 120' (FIGS. 1-7B) and their corresponding elements and components. For example, the control assembly 200a may include an access handle 210a and a retainer 220a, which may respectively secure the access sheath 110a and dilator 120a and may connect together to maintain or fix the relative position and/or orientation of the access sheath 110a and dilator 120a (e.g., the access sheath 110a may tubular, such as including an inside lumen defined by a wall, and the dilator 120a may be sized and shaped to be slidably positioned inside the lumen of the access sheath 110a).

As shown in FIG. 8A, the access handle 210a and retainer 220a may connect together in a similar manner as the access handle 210 and retainer 220 (FIG. 4A). For example, the access handle 210a may include a lip 211a and the retainer 220a may include retention clips 221a that may clamp and/or snap over the lip 211a, thereby securing together the access handle 210a and retainer 220a (as described below in more detail). Generally, the retainer 220a may include any number of retention clips 221a, which may be positioned and/or oriented relative to one another in any number of suitable configurations. In the illustrated embodiment, the control assembly 200a includes two retention clips 221a directly opposing each other (e.g., the retention clips 221*a* may be 180° apart from each other, as measured about a center of the retainer 220*a*).

To decouple or detach the access handle 210*a* and retainer 220*a* from each other, the retainer 220*a* may move outward and/or away from the access handle 210*a* thereby releasing the lip 211*a*. In an embodiment, the retainer 220*a* includes levers 223*a* connected to the retention clips 221*a*. More specifically, operation of the levers 223*a* may move the corresponding retention clips 221*a* (e.g., outward to release the lip 211*a* and/or inward to capture or secure the lip 211*a*). In an embodiment, the retention clips 221*a* may be generally biased, in a manner that without applying external force to the levers 223*a*, the lip 211*a* are positioned and oriented to clamp over the lip 211*a*. Furthermore, applying downward force onto the levers 223*a* (e.g., urging the levers 223*a* toward each other and/or the center of the retainer 220*a*) may correspondingly urge or move the retention clips 221*a* away from each other and/or away from the lip 211*a*, thereby releasing the lip 211*a* and the access handle 210*a* from the retainer 220*a*.

In an embodiment, the retention clips 221*a* and levers 223*a* may be connected to or integrated with corresponding pivot posts 224*a*, which may provide and/or define a pivot point, relative to which the levers 223*a* and corresponding retention clips 221*a* may pivot and move away or toward the lip 211*a* of the access handle 210*a* (e.g., relative to one or more supports, such as supports 225*a*). For example, the pivot posts 224*a* may be suitably resilient, such that at least a portion of the pivot posts 224*a* may bend, thereby producing a suitable deflection or pivoting of the retention clips 221*a* in response to a force applied to the levers 223*a*. Additionally or alternatively, the pivot posts 224*a* may be connected to or integrated with corresponding supports 225*a*. For example, the pivot posts 224*a* may extend outward from the corresponding supports 225*a*. In an embodiment, the pivot posts 224*a* may have ends thereof connected to or integrated with the retention clips 221*a* and/or levers 223*a*. Moreover, pivot posts 224*a* may elastically bend relative to the supports 225*a* (e.g., the supports 225*a* may have a suitable material and/or configuration, such that in response to the force applied on the levers 223*a*, the pivot posts 224*a* bend and/or the supports 225*a* may remain substantially undeformed).

The supports 225*a* may be connected to or integrated with any suitable portions or elements of the retainer 220*a*. For example, the retainer 220*a* may include a guide tube 226*a* extending proximally (e.g., axially relative to centerline of the access sheath 110*a* and/or toward the user or practitioner) from a base 227*a* of the retainer 220*a*. In other words, the tube 226*a* may be connected to or integrated with the base 227*a* of the retainer 220*a*. The supports 225*a* also may be connected to or integrated with the base 227*a* of the retainer 220*a*.

Hence, the retention clips 221*a* may move relative to the base 227*a* and relative to the supports 225*a*, as the pivot posts 224*a* bend and/or deflect. In an embodiment, as described below in more detail, a portion of the retainer 220*a*, which includes the lip 211*a*, may be secured between the retention clips 221*a* and the base 227*a* of the retainer 220*a*. Operation or movement of the retention clips 221*a* toward and away from the lip 211*a* may secure the access handle 210*a* to the retainer 220*a* by clamping or securing a portion of the access handle 210*a* at the lip 211*a* thereof between the retention clips 221*a* and base 227*a* of the retainer 220*a*. In any event, unclamping or moving the retention clips 221*a* away from the lip 211*a* may release the lip 211*a* and access handle 210*a* from the retainer 220*a*; subsequently, the retainer 220*a* may be decoupled or detached from the access handle 210*a*, as described below in more detail.

In one or more embodiments, the access handle 210*a* may include a funnel 213*a* at a proximal end and a distal tip 214*a* at a distal end thereof. In some embodiments, a ribbed section 215*a* may extend between the funnel 213*a* and the distal tip 214*a*. For example, the ribbed section 215*a* may be generally configured to have a suitable flexibility and/or bendability, such that the distal tip 214*a* may move relative to the funnel 213*a*. Additionally or alternatively, the ribbed section 215*a* may be configured to facilitate gripping thereof by a user.

As mentioned above, the access sheath 110*a* may be connected or secured to the access handle 210*a*, and the dilator 120*a* may be connected or secured to the retainer 220*a*. For example, as shown in FIG. 8B, the access handle 210*a* may include a handle pocket 212*a* sized and configured to secure the access sheath 110*a* therein. The access sheath 110*a* may be secured in the handle pocket 212*a* in any number of ways and with any number of suitable mechanisms. In some embodiments, the access sheath 110*a* may be press-fit in the handle pocket 212*a*. Additionally or alternatively, the access sheath 110*a* may be glued, welded, fastened, or otherwise secured in the handle pocket 212*a*, such that the access sheath 110*a* may remain connected or attached to the access sheath 110*a* during use.

Analogously, the retainer 220*a* may include a retainer pocket 222*a* that may secure the dilator 120*a* therein (e.g., in a similar manner as the access handle 210*a* secures the access sheath 110*a*). The dilator 120*a* may be positioned inside the access sheath 110*a* (as described above), and the access sheath 110*a* and dilator 120*a* may be moveable relative to each other. As such, relative movement between the access handle 210*a* and the retainer 220*a* may produce a corresponding relative movement between the access sheath 110*a* and dilator 120*a*. For example, the access handle 210*a* and retainer 220*a* may be detached from each other and the retainer 220*a* together with the dilator 120*a* may more proximally relative to the access handle 210*a*, such that the dilator 120*a* is removed or withdrawn from the access sheath 110*a*.

In some embodiments, the dilator 120*a* may include a channel extending therethrough. For example, a guidewire may be first inserted or advanced to a suitable location in the patient, and the access sheath 110*a*, dilator 120*a*, access handle 210*a*, and retainer 220*a* (assembled together) may be advanced over the guidewire (e.g., the guide tube 226*a* of the retainer 220*a* may be generally tubular and may be aligned with the channel in the dilator 120*a*, such as to facilitate the guidewire passing therethrough and through the channel in the dilator 120*a*). After suitably positioning the access sheath 110*a* and/or the dilator 120*a* in the patient, the guidewire may be withdrawn. Moreover, the retainer 220*a* together with the dilator 120*a* may be removed.

In particular, for example, removal of the retainer 220*a* together with the dilator 120*a* from the access handle 210*a* may expose or provide access to the funnel 213*a*. As described above, any number of suitable tools or instruments may be advanced through the funnel 213*a* and through the access sheath 110*a*. As mentioned above, an exterior of the ribbed section 215*a* may define any suitable number of ribs. In some embodiments, an interior of the ribbed section 215*a* may be generally smooth. For example, the handle pocket 212*a* may be generally cylindrical and may secure a correspondingly cylindrical access sheath 110*a* therein. In one or embodiments, the interior of the ribbed section 215a may provide or form a transition between a flared or generally spherical surface of the funnel 213a and the cylindrical handle pocket 212a or tubular cylinder of the access sheath 110a (e.g., at the proximal portion, the interior of the ribbed section 215a may have an inside diameter that is similar to the inside diameter of the access sheath 110a).

Figure 8C:
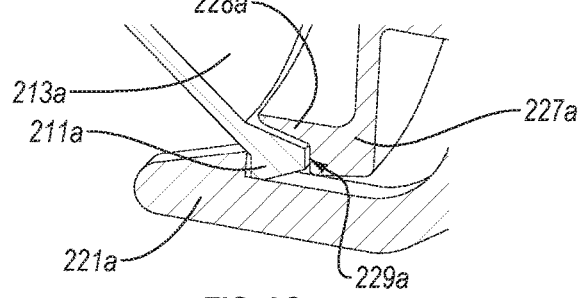
FIG. 8C is an enlarged isometric cutaway view of the sheath-dilator assembly connected to the control handle assembly of FIG. 8B taken from region 8C thereof.

In an embodiment, when the access handle 210a and the retainer 220a are assembled and snapped together, the control assembly 200a formed thereby may have a substantially enclosed space. The enclosed space may be located between and formed by the access handle 210a and the retainer 220a. For example, the enclosed space may be defined by and between the funnel 213a, base 227a, and an interior surface of tapered section 228a (FIG. 8C)

As noted above, a portion of the access handle 210a may be clamped or secured between the retention clips 221a of the retainer 220a. For example, as shown in FIG. 8C, the retainer 220a may include a tapered portion 228a that extends distally from the base 227a (e.g., the tapered portion 228a may have a generally conical shape). It should be appreciated that the taper or angle of the tapered portion 228a may be a locking or a non-locking taper. Moreover, the interior of the lip 211a may have a tapered shape that may correspond to or may be complementary of the tapered shape of the tapered portion 228a of the retainer 220a (e.g., the interior taper of the lip 211a may extend and/or transition from the interior surface of the funnel 213a). In some embodiments, the complimentary tapered shapes of the tapered portion 228a and the interior of the lip 211a may locate and/or orient the access handle 210a relative to the retainer 220a.

In some embodiments, the retainer 220a may include a step 229a extending outward from the tapered section 228a, such that the tapered section 228a is recessed from an outer or peripheral surface of the base 227a, and the step 229a extends from the peripheral surface of the base 227a to outer surface of the tapered section 228a. For example, the step 229a may provide a stop and/or support for a portion of the access handle 210a, such that abutting a portion of the access handle 210a against the step 229a may prevent relative movement of the retainer 220a and the access handle 210a toward each other. Furthermore, in an embodiment, the lip 211a may be clamped or secured by the tapered portion 228a and step 229a on one side and the retention clips 221a on another side, which may collectively prevent or limit movement of the lip 211a relative to the retainer 220a, thereby securing together the access handle 210a and retainer 220a (e.g., one or more portions of the lip 211a may be positioned between and/or at least partially surrounded by the tapered section 228a, an undercutting portions of the clips 221a, and the step 229a). In an embodiment, the outer shape of the tapered section 228a may be generally conical (e.g., may have a shape of a truncated cone).

Figure 9A:
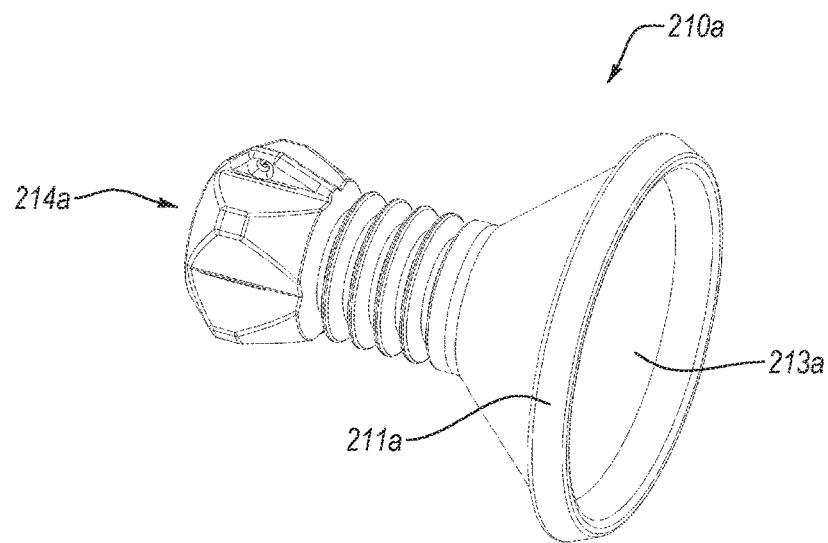
FIG. 9A is an isometric view of an access handle of the control handle assembly of FIGS. 8A-8B.
Figure 9B:
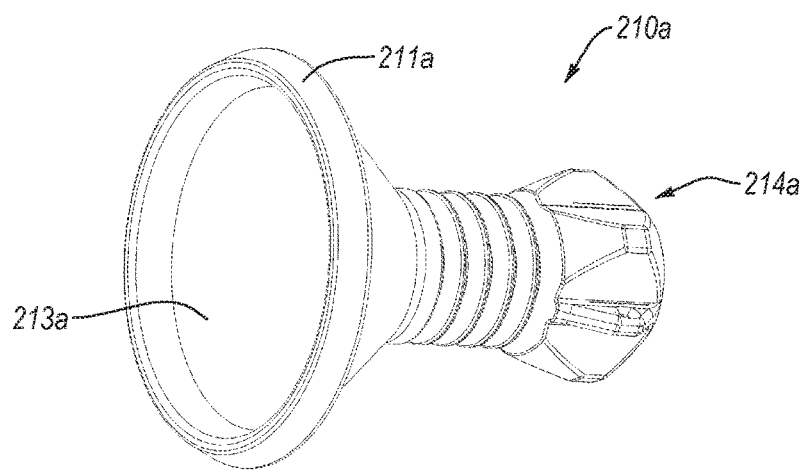
FIG. 9B is another isometric view of an access handle of the control handle assembly of FIGS. 8A-8B.

FIGS. 9A-9B illustrate enlarged isometric views of the access handle 210a. In the illustrated embodiment, the distal tip 214a includes a plurality of peaks (e.g., formed by truncated four-sided pyramids) distributed about a perimeter of the access handle 210a, at the distal end thereof. Moreover, space between the four-sided pyramids may form troughs, which may be distributed about the perimeter of the access handle 210a in a similar manner as the four-sided pyramids or peaks. For example, the troughs may facilitate gripping the access handle 210a at the distal tip 214a.

As described above, the access handle 210a may include the lip 211a. In some embodiments, the lip 211a is substantially uninterrupted and spans the entire perimeter of the access handle 210a. Alternatively or additionally, the access handle 210a may include multiple lips that may span about some of or the entire perimeter of the access handle 210a. In any event, one or more lips of the access handle 210a may be positioned and/or oriented in a manner that facilitates engagement thereof by corresponding retention clips of the retainer, as described above.

Figure 10A:
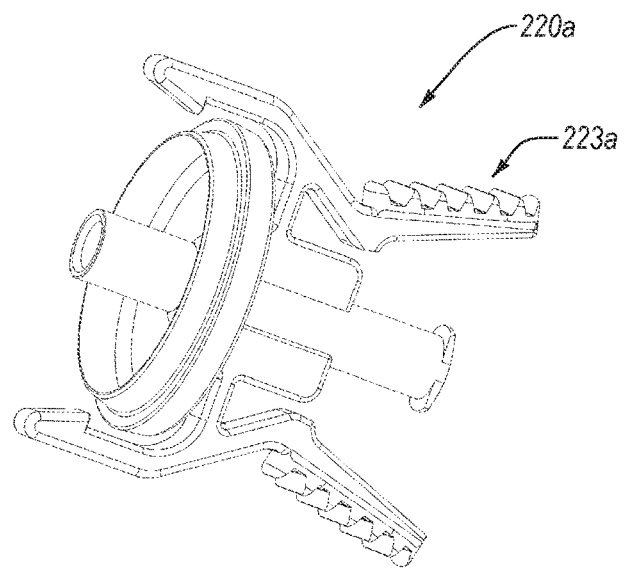
FIG. 10A is an isometric view of a retainer of the control handle assembly of FIGS. 8A-8B.
Figure 10B:
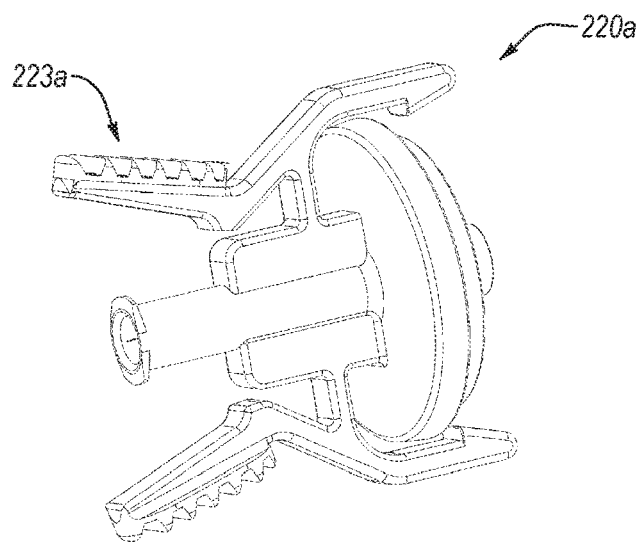
FIG. 10B is an isometric view of a retainer of the control handle assembly of FIGS. 8A-8B.

FIGS. 10A-10B illustrate enlarged isometric views of the retainer 220a. In the illustrated embodiment, the levers 223a of the retainer 220a include multiple ribs. For example, the ribs may facilitate gripping and/or squeezing of the levers 223a during use. It should be appreciated that the levers 223a may include any number of gripping features or no gripping features, and the gripping features may vary from one embodiment to the next.

Generally, any suitable access sheath and/or dilator may be connected to the access handle 210a and/or retainer 220a. Moreover, as described above, the access sheath and dilator may be adjustable to a suitable or desired length. Alternatively, in one or more embodiments, the access sheath and/or dilator may be prefabricated to have a fixed length.

Figure 11A:
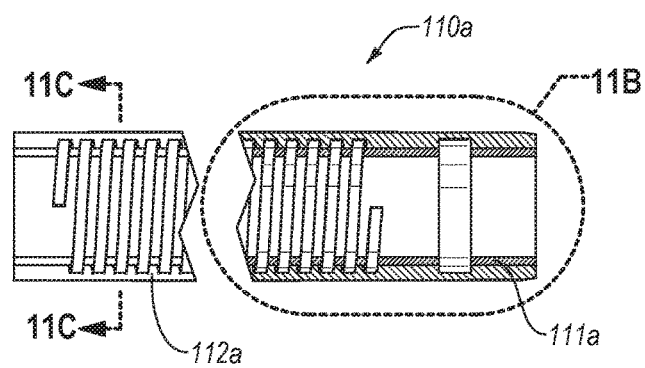
FIG. 11A is a longitudinal cutaway view of an access sheath, according to an embodiment.
Figure 11B:
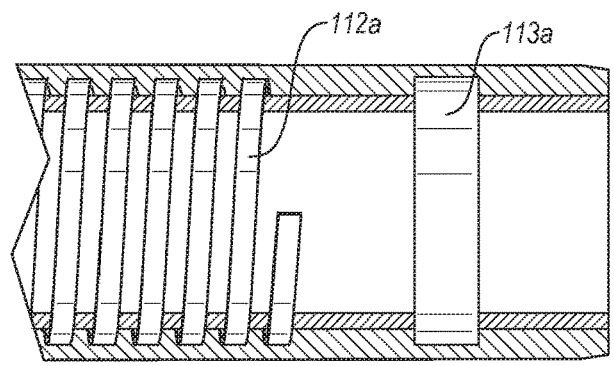
FIG. 11B is an enlarged longitudinal cutaway view of the access sheath of FIG. 11A.
Figure 11C:
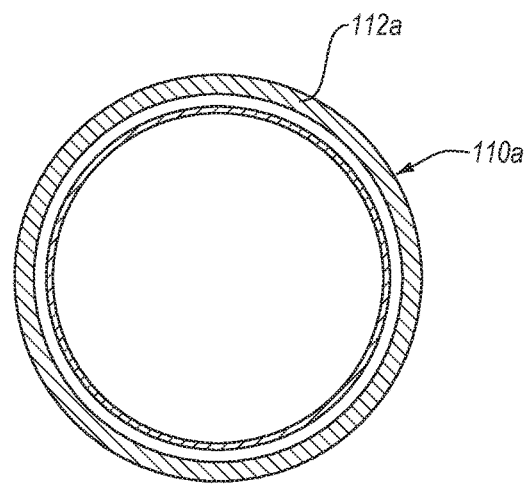
FIG. 11C is a transverse cross-sectional view of the access sheath of FIG. 11A taken along section B-B.

FIGS. 11A-11C illustrate the access sheath 110a according to an embodiment. More specifically, the access sheath 110a may have a generally tubular shape defined by a generally cylindrical wall 111a of the access sheath 110a. For example, the wall 111a of the access sheath 110a may comprise one or more polymeric materials (e.g., Polyurethane, Polyether block amide (PEBAX), Polytetrafluoroethylene (PTFE), etc.). In some embodiments, an outer portion of the wall 111a may comprise a first material (e.g., PEBAX) and an inner portion of the wall may comprise a second, different material (e.g., PTFE). Moreover, in some embodiments, the access sheath 110a may include one or more reinforcement members 112a (e.g., coils, such as stainless steel coils), which may extend and/or may be positioned along the length of the access sheath 110a. Moreover, in at least one embodiment, the access sheath 110a includes a radiopaque marker 113a, which may be positioned at or near a distal end of the access sheath 110a.

Generally, the size and length of the access sheath 110a may vary from one embodiment to another. In some embodiments, the access sheath 110a may have one or more of the following sizes (denoted as inside diameter/outside diameter): 10/12 Fr, 12/14 Fr., 13/15 Fr, etc. It should be appreciated that in some embodiments, the access sheath 110a may be smaller than 10/12 Fr or larger than 13/15 Fr. The access sheath 110a also may have any suitable length, such as 25 cm, 35 cm, 45 cm, etc. It should be appreciated that the access sheath 110a may be shorter than 25 cm or longer than 45 cm.

Figure 12A:
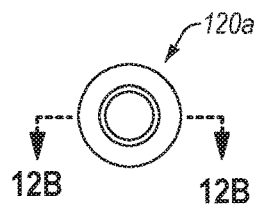
FIG. 12A is a front elevational view of a dilator according to an embodiment.
Figure 12B:
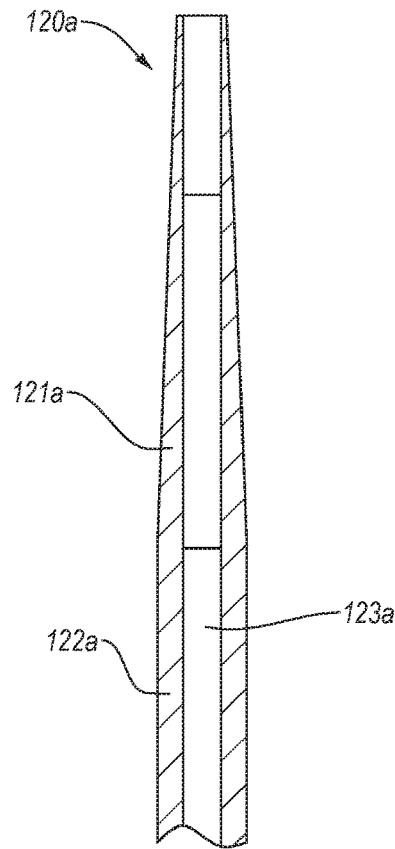
FIG. 12B is a cross-sectional view of the dilator of FIG. 12A take along plane 12B-12B.

As described above, the access sheath 110a may be fitted or positioned over a suitable dilator, which may facilitate advancement of the access sheath 110a to the target location in the patient. FIGS. 12A-12B illustrate the dilator 120a according to at least one embodiment. In particular, for example, the dilator 120a includes a tapered distal portion 121a, which may spread tissue and facilitate advancement of the dilator 120a to target location. The dilator 120a also may include a generally cylindrical portion 123a, which may extend from a proximal end of the dilator 120a to the tapered distal portion 121a thereof. In some embodiments, when the access sheath is fitted over the dilator 120a, the tapered distal portion 121a and/or some of the cylindrical portion 123a of the dilator 120a may extend past the distal end of the access sheath.

The outside diameter of the cylindrical portion 123a may be similar to the inside diameter of the access sheath fitted over the dilator 120*a* (e.g., the outside diameter of the cylindrical portion 123*a* may be smaller than the inside diameter of the access sheath by an amount ranging from 1% to 10% of the inside diameter of the access sheath). In one or more embodiments, the dilator 120*a* may include a through channel 123*a* (e.g., extending from the proximal end to the distal end of the dilator 120*a*). As mentioned above, the dilator 120*a* may be advanced over a guidewire, such that the guidewire passes into and through the channel 123*a*.

Figure 13A:
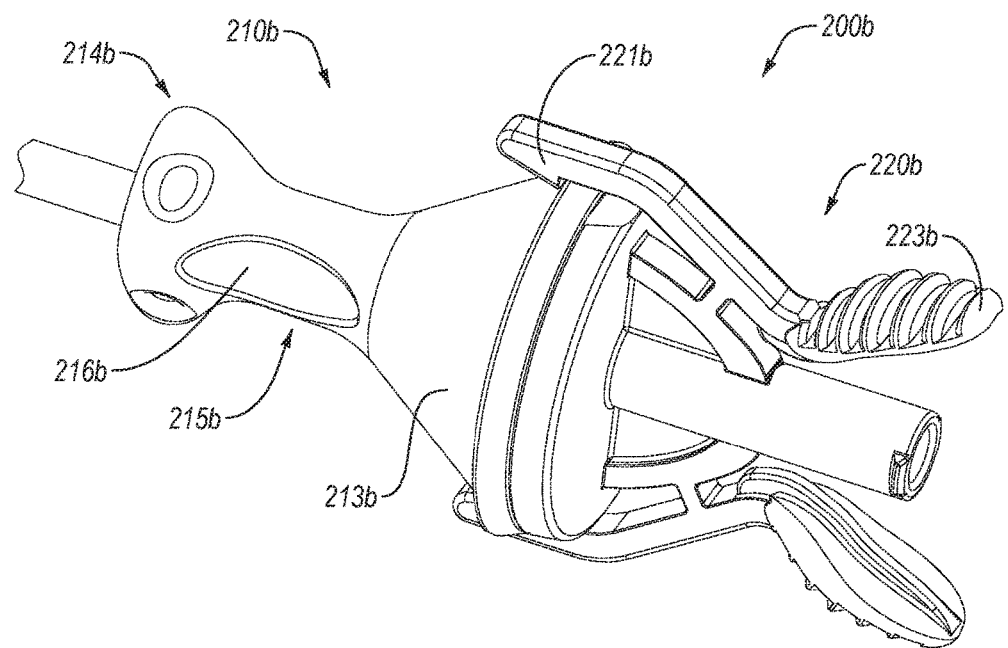
FIG. 13A is an isometric view of a control handle assembly, according to an embodiment.
Figure 13B:
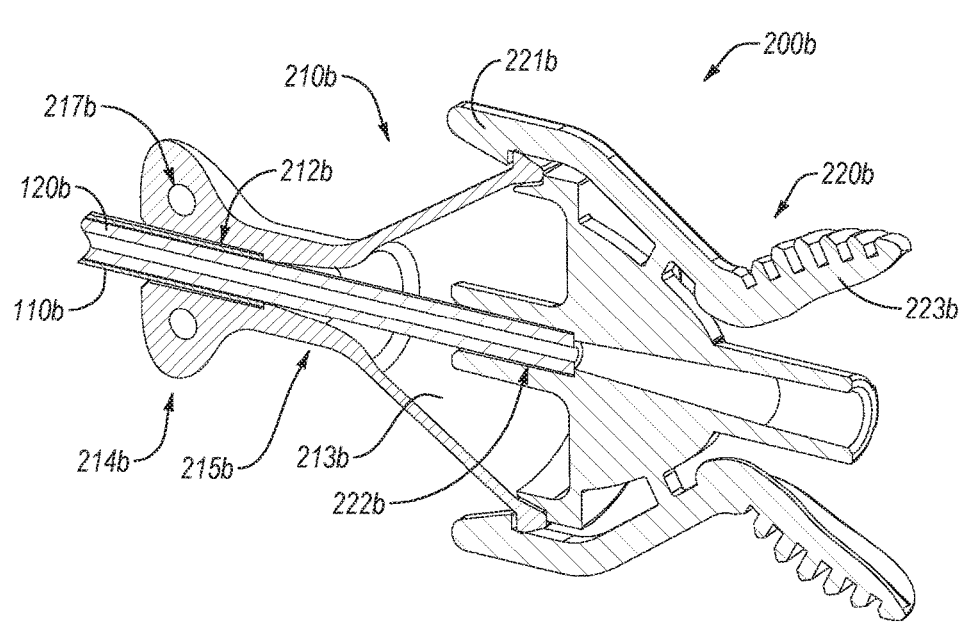
FIG. 13B is an isometric cutaway view of the control handle assembly of FIG. 13A.

It should be appreciated that the general shape (e.g., external shape) of the control assembly and/or elements or components thereof may vary from one embodiment to the next (e.g., without appreciably altering general function, arrangement, configuration, or combination thereof for such modified elements or components). FIGS. 13A-13B illustrate a control assembly 200*b* that includes an access handle 210*b* and a retainer 220*b* connectable together according to an embodiment. In the illustrated embodiment, the access handle 210*b* and retainer 220*b* are connected together. As described above, however, the access handle 210*b* may be disconnected from and/or reconnected to the retainer 220*b*. In any event, except as otherwise described herein, the control assembly 200*b* and its elements and components may be similar to or the same as the control assembly 200 (FIGS. 1-7B) and/or the control assembly 200*a* (FIGS. 8A-10B) and their respective elements or components.

For example, the access handle 210*b* and/or the retainer 220*b* of the control assembly 200*b* may be similar to the access handle 210*a* and retainer 220*a*, respectively, of the control assembly 200*a* (FIGS. 8A-10B). In an embodiment, the access handle 210*b* includes a lip 211*b*, and the retainer 220*b* includes retention clips 221*b* that may snap or clamp over the lip 211*b*, thereby securing or connecting together the access handle 210*b* and retainer 220*b*. For example, as described above, the retention clips 221*b* may be operated by levers 223*b* of the retainer 220*b* (e.g., to release and/or to clamp the access handle 210*b* to the retainer 220*b*).

In some embodiments, the access handle 210*b* has a funnel 213*b*, a distal tip 214*b*, and an intermediate section 215*b* that spans therebetween. For example, the exterior of the intermediate section 215*b* may be generally shaped to transition from the exterior shape of the funnel 213*b* to the exterior shape of the distal tip 214*b*. Moreover, the intermediate section 215 may facilitate gripping the access handle 210*b* by a user (e.g., the intermediate section 215*b* may define a recess between exterior surface of the funnel 213*b* and the outer surface defining the distal tip 214*b*). For example, the intermediate section 215*b* may include one or more indents 216*b* (e.g., the indents 216*b* may be sized and configured for positioning a finger, such as a thumb, therein).

In at least one embodiment, the distal tip 214*b* may have a generally rounded shape (e.g., the distal tip 214*b* may have an approximately oval shape). The access handle 210*b* may secure an access sheath 110*b*, while the retainer 220*b* may secure a dilator 120*b* (e.g., the access handle 210*b* may include a handle pocket 212*b*, and the retainer 220*b* may include a retainer pocket 222*b*, which may secure respective access sheath 110*b* and dilator 120*b*). For example, as described above, the access sheath 110*b* and/or the dilator 120*b* may be press-fit in the respective handle pocket 212*b* and handle pocket 212*b*. In some embodiment, the access handle 210*b* and/or retainer 220*b* may include multiple portions (e.g., two generally opposing and/or complementary halves, which may be mirror images of each other), which may be connected together to secure the respective access sheath 110*b* and dilator 120*b* in the handle pocket 212*b* and retainer pocket 222*b*. For example, the access handle 210*b* may include fastener openings 217*b*, which may accept corresponding fasteners (e.g., rivets, screws, etc.) that may connect together the opposing halves of the access handle 210*b*. Additionally or alternatively, the opposing halves may be welded, glued, or otherwise secured together. Moreover, connecting together the opposing halves of the access handle 210*b* may secure the access sheath 110*b* in the handle pocket 212*b* of the access handle 210*b*.

The retainer 220*b* may include multiple portions that may be connected together to form the retainer 220*b*. In some embodiments, connecting together the multiple portions of the retainer 220*b* may secure the dilator 120*b* in the retainer pocket 222*b*. Additionally or alternatively, the access sheath 110*b* and/or dilator 120*b* may be welded (e.g., ultrasonically welded) in and/or to the respective handle pocket 212*b* and retainer pocket 222*b*. For example, the access sheath 110*b* and/or the dilator 120*b* may be welded while one or more portions of multi-portion access handle 210*b* and/or retainer 220*b* are at least partially detached one from another. In one or more embodiments, the access handle 210*b* and/or the retainer 220*b* may be overmolded over the respective access sheath 110*b* and/or dilator 120*b*, thereby securing the access sheath 110*b* and/or dilator 120*b* in the respective handle pocket 212*b* and retainer pocket 222*b*.

While various aspects and embodiments have been disclosed herein, other aspects and embodiments are contemplated. The various aspects and embodiments disclosed herein are for purposes of illustration and are not intended to be limiting.

What is claimed is:

1. An access system, comprising:
   an access handle including:
   a wall including an interior surface defining a funnel having an opening at a proximal end of the access handle; and
   a lip positioned near the opening of the funnel and extending outward from an exterior surface of the wall;
   a tubular access sheath secured to the access handle;
   a retainer including:
   a base;
   a plurality of clips operably connected to the base, the plurality of clips being sized and configured to clamp about the lip of the access handle; and
   a tapered section that has a generally conical shape and extends outward in a distal direction from the base; and
   a dilator sized and shaped to be positioned inside the access sheath, the dilator being secured to the retainer;
   wherein, when assembled, the lip is clamped or secured by the tapered section on one side and the plurality of clips on another side.

2. The access system of claim 1, wherein the retainer includes one or more supports, a plurality of pivot posts connected to or integrated with the one or more supports, and each of the plurality of clips is connected to or integrated with corresponding pivot post of the plurality of pivot posts and is pivotable relative to the one or more supports.

3. The access system of claim 2, wherein the retainer includes a plurality of levers each of which is connected to or integrated with a corresponding pivot post of the plurality of pivot posts and configured to pivot the plurality of clips relative to the one or more supports.

4. The access system of claim 2, wherein the one or more supports are connected to or integrated with the base.

5. The access system of claim 4, wherein the one or more supports extend in a proximal direction from the base.

6. The access system of claim 4, wherein the tapered section extending radially about the dilator.

7. The access system of claim 6, wherein the tapered section includes an outer surface that has a generally conical shape.

8. The access system of claim 1, wherein the access handle includes a tapered portion that is configured substantially complementary to the tapered section of the retainer.

9. The access system of claim 8, wherein the tapered portion of the access handle is defined by another interior surface that extends proximally from the interior surface that defines the funnel.

10. The access system of claim 1, wherein the retainer includes a step extending from a peripheral surface of the base to an outer surface defining the tapered section.

11. The access system of claim 10, wherein one or more portions of the lip of the access handle are positioned between the tapered section, the step, and the one or more clips of the plurality of clips.

12. The access system of claim 1, wherein the access handle includes a first portion and a second portion connected together by one or more fasteners.

13. The access system of claim 1, wherein the access sheath includes one or more indicators located along a length thereof and configured to facilitate length-adjusting the access sheath to a selected length.

14. The access system of claim 13, wherein the one or more indicators include at least one of markings, patterns, indents, or protrusions.

15. The access system of claim 13, wherein the access sheath includes a plurality of reinforcing cores encapsulated in a wall forming an inside surface and an outer surface of the access sheath.

16. The access system of claim 15, wherein the one or more indicators are located at positions between adjacent ones of the plurality of reinforcing cores.

17. The access system of claim 1, wherein the access handle includes a generally rounded distal tip and an intermediate section extending between the generally rounded distal tip and the funnel and defining a recess between an outer surface of the funnel and an outer surface defining the distal tip.

18. An access assembly, comprising:
an access handle including:
a wall including an interior surface defining a funnel having an opening at a proximal end of the access handle; and
a lip positioned near the opening of the funnel and extending outward from an exterior surface of the wall;
a tubular access sheath secured to the access handle;
a retainer including:
a base;
a plurality of clips operably connected to the base, the plurality of clips and positioned about the lip and detachably securing the retainer to the access handle; and
a tapered section that has a generally conical shape and extends outward in a distal direction from the base; and
a dilator secured to the retainer and slidably positioned inside the access sheath;
wherein, when assembled, the lip is clamped or secured by the tapered section on one side and the plurality of clips on another side.

19. The access system of claim 18, wherein the retainer includes a base portion, and the interior surface defining the funnel and the base portion of the retainer at least partially define an enclosed space between the access handle and the retainer.

20. An access system, comprising:
an access handle including:
a wall including a first interior surface defining a funnel having an opening at a proximal end of the access handle and a second interior surface extending proximally from the first interior surface; and
a lip positioned near the opening of the funnel and extending outward from an exterior surface of the wall;
a tubular access sheath secured to the access handle;
a retainer including:
a base;
a plurality of clips operably connected to the base, the plurality of clips being sized and configured to clamp about the lip of the access handle; and
an outer surface extending distally relative to the base, the outer surface having a complementary size and shape to the second interior surface of the wall of the access handle; and
a dilator sized and shaped to be positioned inside the access sheath, the dilator being secured to the retainer.

21. The access system of claim 20, wherein the second interior surface of the wall of the access handle and the outer surface of the retainer have substantially complementary tapers.

22. The access system of claim 21, wherein the second inner surface of the wall of the access handle is substantially continuous.

23. The access system of claim 21, wherein the outer surface of the retainer defines a generally conical shape.

24. The access system of claim 20, wherein the access handle and the retainer define a substantially enclosed space therebetween.

25. The access system of claim 20, wherein the retainer includes a step extending radially outward from the outer surface of the retainer.

26. The access system of claim 25, wherein the access handle includes a step surface extending radially outward from the second inner surface of the wall, the step surface being configured to be positioned near the step of the retainer when the plurality of clips of the retainer clamp about the lip of the access handle.

27. An access system, comprising:
an access handle including:
a wall including an outer surface and an interior surface defining a funnel having an opening at a proximal end of the access handle; and
a lip positioned near the opening of the funnel and extending outward from an exterior surface of the wall;
a distal tip including an outer surface; and
an intermediate section extending between the distal tip and the funnel and defining a recess between the outer surface of the funnel and the outer surface defining the distal tip;
a tubular access sheath secured to the access handle;
a retainer including a plurality of clips and a tapered section, the plurality of clips sized and configured to clamp about the lip of the access handle, the tapered section extending outward in a distal direction; and
a dilator sized and shaped to be positioned inside the access sheath, the dilator being secured to the retainer;

wherein, when assembled, the lip is clamped or secured by the tapered section on one side and the plurality of clips on another side.

28. The access system of claim 27, wherein the access handle includes a first portion and a second portion connected together by one or more fasteners.

29. The access system of claim 27, wherein the distal tip of the access handle is generally rounded.

30. The access system of claim 27, wherein the retainer includes one or more supports, a plurality of pivot posts connected to or integrated with the one or more supports, and each of the plurality of clips is connected to or integrated with a corresponding pivot post of the plurality of pivot posts and is pivotable relative to the one or more supports.

31. The access system of claim 30, wherein the retainer includes a plurality of levers each of which is connected to or integrated with a corresponding pivot post of the plurality of pivot posts and configured to pivot the plurality of clips relative to the one or more supports.

32. The access system of claim 30, wherein the retainer includes a base and the one or more supports are connected to or integrated with the base.

33. The access system of claim 32, wherein the one or more supports extend in a proximal direction from the base.

34. The access system of claim 32, wherein the tapered section has a generally conical shape.

35. The access system of claim 32, wherein the access handle includes a tapered portion that is configured substantially complementary to the tapered section of the retainer.

36. The access system of claim 35, wherein the tapered portion of the access handle is defined by another interior surface that extends proximally from the interior surface that defines the funnel.

37. The access system of claim 36, wherein the retainer includes a step extending from a peripheral surface of the base to an outer surface defining the tapered section.

38. The access system of claim 37, wherein one or more portions of the lip of the access handle are positioned between the tapered section, the step, and the one or more clips of the plurality of clips.

39. The access system of claim 27, wherein the access sheath includes one or more indicators located along a length thereof and configured to facilitate length-adjusting the access sheath to a selected length.

40. The access system of claim 39, wherein the one or more indicators include at least one of markings, patterns, indents, or protrusions.

* * * * *